United States Patent
Murthy et al.

(10) Patent No.: US 7,033,599 B2
(45) Date of Patent: Apr. 25, 2006

(54) INJECTABLE COMPOSITIONS FOR THE CONTROLLED DELIVERY OF PHARMACOLOGICALLY ACTIVE COMPOUND

(75) Inventors: Yerramilli V.S.N. Murthy, Apex, NC (US); Robert H. Suva, Windham, ME (US)

(73) Assignee: Idexx Laboratories Inc., Westbrook, ME (US)

( * ) Notice: Subject to any disclaimer, the term of this patent is extended or adjusted under 35 U.S.C. 154(b) by 321 days.

(21) Appl. No.: 10/403,100

(22) Filed: Mar. 28, 2003

(65) Prior Publication Data
US 2005/0075296 A1  Apr. 7, 2005

Related U.S. Application Data

(63) Continuation of application No. 10/274,445, filed on Oct. 18, 2002.

(60) Provisional application No. 60/343,625, filed on Oct. 19, 2001.

(51) Int. Cl.
*A61K 9/00* (2006.01)

(52) U.S. Cl. ............... 424/400; 51/37; 51/39; 51/152

(58) Field of Classification Search ........... 424/400; 514/37, 39, 152
See application file for complete search history.

(56) References Cited

U.S. PATENT DOCUMENTS

| 4,298,375 A | 11/1981 | Howe et al. |
| 4,820,695 A | 4/1989 | Debono et al. |
| 5,574,020 A * | 11/1996 | Klink et al. ............ 514/30 |
| 5,723,447 A | 3/1998 | Macy et al. |

(Continued)

FOREIGN PATENT DOCUMENTS

JP  2-7314  7/1982

(Continued)

OTHER PUBLICATIONS

Jordan, WH et al., "A Review of the Toxicology of the Antibiotic MICOTIL 300," *Vet Hum Toxicol* 35(2):151-158 (Apr. 1993).

(Continued)

*Primary Examiner*—Alton Pryor
*Assistant Examiner*—Konata M. George
(74) *Attorney, Agent, or Firm*—Kenyon & Kenyon (57) ABSTRACT

The present invention provides compositions and methods for extending the release times and lowering the toxicity of pharmacologically active compounds. The compounds comprise a salt of the pharmacologically active compound with a lipophilic counterion and a pharmaceutically acceptable water soluble solvent combined together to form an injectable composition. The lipophilic counterion may be a saturated or unsaturated $C_8$–$C_{22}$ fatty acid, and preferably may be a saturated or unsaturated $C_{10}$–$C_{18}$ fatty acid. When injected into a mammal, at least a portion of the composition precipitates and releases the active compound over time. Thus, the composition forms a slowly releasing drug depot of the active compound in the mammal. Therefore, the present invention enables one to provide a controlled dose administration of the active compound for a periods of up to 15 days or even longer. Many compounds can be administered according to the present invention including, but not limited to, tilmicosin, oxytetracycline, metoprolol, fluoxetine, roxithromycin, and turbinafine.

48 Claims, 10 Drawing Sheets

U.S. PATENT DOCUMENTS

| | | |
|---|---|---|
| 5,747,058 A | 5/1998 | Tipton et al. |
| 5,958,888 A | 9/1999 | Macy et al. |
| 6,034,070 A | 3/2000 | Armbruster |
| 6,074,657 A | 6/2000 | Brown |
| 6,110,905 A | 8/2000 | Patterson et al. |
| 6,239,112 B1 | 5/2001 | Macy et al. |
| 6,310,053 B1 | 10/2001 | Patterson et al. |
| 6,328,961 B1 | 12/2001 | Cutrone et al. |
| 6,403,057 B1 | 6/2002 | Schneider et al. |
| 6,504,005 B1 | 1/2003 | Fridkin et al. |
| 6,660,278 B1 | 12/2003 | Larsson et al. |

FOREIGN PATENT DOCUMENTS

| | | |
|---|---|---|
| JP | 2-7314 | 1/1990 |

OTHER PUBLICATIONS

Jordan, WH et al., "A Review of the Toxicology of the Antibiotic MICOTIL 300," *Vet Hum Toxical* 35(2): 151-158 (Apr. 1993).

International Search Report, dated Apr. 23, 2003, for PCT International Application No. PCT/US02/33300.

\* cited by examiner

INJECTABLE COMPOSITIONS FOR THE CONTROLLED DELIVERY OF PHARMACOLOGICALLY ACTIVE COMPOUND

This application is a continuation of U.S. application Ser. No. 10/274,445, filed Oct. 18, 2002, which claims the benefit of U.S. application Ser. No. 60/343,625, filed Oct. 19, 2001, both of which are hereby incorporated by reference in their entireties including all tables, figures, and claims.

FIELD OF THE INVENTION

The present invention relates to methods and compositions for extending the release times and decreasing the toxicity of pharmacologically active compounds.

BACKGROUND OF THE INVENTION

The following discussion of the background of the invention is merely provided to aid the reader in understanding the invention and is not admitted to describe or constitute prior art to the present invention.

It is often desirable to extend the release time of an injected drug to increase its duration of action, or to reduce its toxic effects. Formulations that are readily soluble in the body are usually absorbed rapidly and provide a sudden burst of available drug as opposed to a more desirable and gradual release of the pharmacologically active product. A variety of attempts have been made to provide controlled and extended release pharmaceutical compounds, but have not succeeded in overcoming all of the problems associated with the technology, such as achieving an extended release time, maximum stability and efficacy, reduced toxicity, maximum reproducibility in preparation, and the elimination of unwanted physical, biochemical, or toxicological effects introduced by undesirable matrix materials.

Oxytetracycline is a widely used and useful antibiotic for treating various infections in mammals. In particular it is used for treating and preventing respiratory infections in domestic animals. There are significant costs associated with repeated administrations through conventional means.

Tilmicosin is a macrolide antibiotic with two tertiary amines. It has a long tissue half-life and is effective against a broad range of bacteria and is used to treat respiratory diseases in cattle. At elevated levels tilmicosin is cardiotoxic and its use in sensitive species such as cats, goats, pigs and horses has been avoided almost entirely due to safety reasons. The commercial product, Micotil® (Eli Lilly & Co., Indianapolis, Ind.), is a solution of the di-phosphate salt and is described in U.S. Pat. No. 5,574,020. This formulation is effective in cattle, but the antibiotic is released rapidly and results in toxicity in many species, including dogs and cats.

SUMMARY OF THE INVENTION

The present invention provides compositions and methods for extending the release times and lowering the toxicity of pharmacologically active compounds. The compounds comprise a salt of the pharmacologically active compound with a lipophilic counterion and a pharmaceutically acceptable water soluble solvent combined together to form an injectable composition. The lipophilic counterion may be a saturated or unsaturated $C_8$–$C_{22}$ fatty acid, and preferably may be a saturated or unsaturated $C_{10}$–$C_{18}$ fatty acid. When injected into a mammal, at least a portion of the composition precipitates and releases the active compound over time. Thus, the composition forms a slowly releasing drug depot of the active compound in the mammal. Therefore, the present invention enables one to provide a controlled release administration of the active compound for periods of 15 days or even longer. In preferred embodiments, the pharmacologically active compound may be tilmicosin, an antibiotic such as oxytetracycline or doxycycline, or fluoxetine, roxithromycin, terbinafine, or metoprolol and the lipophilic counterion may be decanoic acid, lauric acid, oleic acid, linoleic acid, or myristic acid. In preferred embodiments, the pharmaceutically acceptable solvent is N-methyl pyrrolidone (NMP). In another embodiment, the pharmaceutically acceptable solvent is, propylene glycol (e.g., at about 10%) in glycerol formal with or without stabilizers.

The present invention also provides novel methods of administering compositions and formulations of the present invention to mammals. The methods provide compositions of active compounds that, if presented in presently available forms, may result in toxicity to the treated mammal. Thus, the formulations and methods of the present invention enable one to administer compounds that previously have not been able to be widely used in particular species due to safety considerations. The methods also enable one to extend the release times of compounds and provide a controlled dose of active compound to the treated patient. The methods of the present invention enable one to administer the pharmacologically active compound to the treated mammal in a pharmaceutically effective amount for 4–15 days, including any specific number of days up to and including 15 days, or even more. The precise time will depend on several variables that may be manipulated to optimize the present invention for a particular pharmacologically active compound or application. Preferably the compound is present in the treated tissue 4–5 days after injection; and more preferably the compound is present in the treated tissue in a pharmaceutically effective amount 6 days, or even 7 days after injection. In other embodiments, it may also be desirable to manipulate variables so as to extend release times even further than 15 days.

In one aspect, the present invention provides compositions for administration of pharmacologically active compounds. The compositions may comprise a salt of the pharmacologically active compound with a lipophilic counterion and a pharmaceutically acceptable water soluble solvent, combined together under conditions to form an injectable composition. The composition may precipitate and release the pharmacologically active compound over time when injected into the mammal. In various embodiments, the composition of the present invention may comprise a wide variety of pharmacologically active compounds such as tilmicosin, oxytetracycline, doxycycline, metoprolol, sulfamethazine, trimethoprim, neomycin, streptomycin, gentamycin, dibucaine, bupivacaine, benzocaine, tetracaine, acepromazine, itraconazole, tetracyclines, sulfonamides, aminoglycosides, or any pharmacologically active compound with appropriate solubility and chemical functionalities. The lipophilic counterion may be a saturated or unsaturated fatty acid of any specific number of carbons between 8 and 22, preferably a $C_8$–$C_{18}$ fatty acid, and more preferably a $C_{10}$–$C_{18}$ fatty acid, such as lauric acid, linoleic acid, decanoic acid, and myristic acid. Other lipophilic counterions may also be used, for example dicarboxylic acids, such as sebacic acid, polymeric acids, such as lipophilic poly-carboxylic acids, and aromatic acids, such as benzoic acid. The pharmaceutically acceptable carrier may be an organic solvent. In preferred embodiments, the solvent may be pyrrolidone, N-methyl pyrrolidone, polyethylene glycol, propylene glycol, glycerol formal, isosorbid dimethyl ether, ethanol, dimethyl sulfoxide, tetrahydrofurfuryl alcohol, triacetin, or any combination of these, or another solvent found to have similar acceptable properties such as being non-toxic and soluble in water.

In another embodiment the compositions of the invention are a salt of a pharmacologically active compound with a polycarboxylic acid counterion and a pharmaceutically acceptable water soluble solvent, combined together under conditions to form an injectable composition that precipitates when injected into water at room temperature or precipitates in physiological ("in vivo") environments. The composition releases the active compound over time when injected into a mammal. By "polycarboxylic acid" is meant a molecule containing at least two carboxyl groups. In preferred embodiments the polycarboxylic acid is polyaspartic acid, polyacrylic acid, sebacic acid, polysebacic acid, polybenzoic acid, or combinations thereof. By "poly" is meant two or more.

In one embodiment, the pharmacologically active compound may be oxytetracycline, the lipophilic counterion may be lauric acid, and the pharmaceutically acceptable solvent may be propylene glycol, polyethylene glycol, glycerol formal, or an appropriate combination of these. In another embodiment the pharmacologically active compound may be tilmicosin, the lipophilic counterion may be lauric acid, and the pharmaceutically acceptable solvent may be propylene glycol, polyethylene glycol, glycerol formal, or an appropriate combination of these. In still another embodiment, the compositions may precipitate and release the active compound over time when introduced or injected into an aqueous environment. The compositions may also form a drug depot in the mammal when injected, which releases the compound over time.

In another aspect, the present invention provides methods of administering a pharmacologically active compound to a mammal. The methods may comprise preparing a composition of a salt of the pharmacologically active compound with a lipophilic counterion, and a pharmaceutically acceptable water soluble solvent, combined together under conditions to form an injectable formulation, and injecting the composition into the mammal. At least a portion of the composition precipitates and releases the pharmacologically active compound over time when injected into the mammal.

In another aspect, the present invention provides methods of extending the release time of a pharmacologically active compound administered to a mammal. The methods may comprise preparing a formulation of a salt of the pharmacologically active compound with a lipophilic counterion, and a pharmaceutically acceptable water soluble solvent, combined together under conditions to form an injectable formulation, and injecting the composition into the mammal, at least a portion of the composition precipitating and releasing the pharmacologically active compound over time after injection into the mammal, thereby extending the release time of the compound. The invention may therefore provide a controlled dosage of active compound to the treated mammal.

In yet another aspect, the present invention provides methods of manufacturing an injectable formulation for the administration of a pharmacologically active compound to a mammal. The methods may comprise forming a salt of the pharmacologically active compound with a lipophilic counterion, providing water soluble pharmaceutically acceptable solvent, combining the salt and the solvent under conditions to form an injectable formulation, wherein at least a portion of the formulation precipitates and releases the pharmacologically active compound over time when injected into the mammal.

In another aspect the present invention provides compositions for the administration of a pharmacologically active compound to a mammal. The compositions contain a salt of the pharmacologically active compound with a lipophilic counterion and a pharmaceutically acceptable: solvent, combined together to form an injectable composition. At least a portion of the pharmaceutically active compound with lipophilic counterion dissolved in the solvent precipitates in vivo and releases the active compound over time when injected into the mammal.

The present invention therefore offers important advantages over formulations previously available. The present invention allows for the controlled release of pharmacologically active compounds to reduce toxicity, particularly in small animals such as dogs and cats. It also offers the advantage of being able to administer compounds to domestic animals in an efficient manner, thereby requiring a smaller investment in time and resources than is available with previous modes of drug administration. The pharmacologically active compound is available in a stable, injectable, formulation that precipitates when injected and slowly releases the active compound over an extended period of time.

The summary of the invention described above is not limiting and other features and advantages of the invention will be apparent from the following detailed description of the preferred embodiments, as well as from the claims.

DETAILED DESCRIPTION OF THE INVENTION

The compositions of the present invention may be prepared using salts of pharmacologically active compounds with basic functionalities. These can be made using a variety of lipophilic acids, saturated or unsaturated fatty acids, cholic acids, phosphatidic acids, dicarboxylic acids such as sebacic acid or any acid that, when combined with the pharmacologically active compound, renders the resulting salt insoluble in water, but soluble in a water soluble solvent. By "salt" is meant two compounds that are not covalently linked but are chemically bound through ionic attractions. By "water miscible" is meant that the solvent is capable of mixing in any ratio in water without separation of two phases. By "water soluble" is meant that the solvent has some significant level of solubility in aqueous solutions, e.g., triacetin is considered a water soluble solvent since it is soluble in water at a ratio of about 1:14. By a "lipophilic counterion" is meant an ionic form of a fat soluble molecule. The lipophilic counterion may preferably be a fatty acid, but may also be another fat soluble molecule. The counterion has at least one charge opposite to that of a chemical group on an opposing salt member, thereby causing an ionic attraction between the two molecules. By "injectable formulation" or "injectable composition" is meant a formulation or composition that can be drawin into a syringe and injected subcutaneously, intraperitoneally, or intramuscularly into a mammal without causing adverse effects due to the presence of solid materials in the composition. Solid materials include, but are not limited to, crystals, a gummy mass, and a gel. By "pharmacologically active compound" is meant a chemical compound that causes a pharmacological effect in the treated mammal. For example, the effect may be to destroy or prevent growth of bacteria or parasites, reduce inflammation, or another pharmaceutical and measurable effect in the treated mammal.

By the verb "precipitate" is meant that the compound forms a precipitate, or solid. A precipitate is an insoluble solid formed in solution at room temperature in vitro or in a physiological (in vivo) environment. The precipitate can take many forms such as, for example, a solid, a crystal, a gummy mass, or a gel. By "pharmaceutically effective amount" is meant an amount that exerts a measurable and medically significant effect on the treated mammal, resulting in progress towards curing or preventing the subject disease, or alleviating or preventing the condition that was the reason for treatment. A "pharmaceutically acceptable solvent" is a liquid that dissolves a salt of the pharmacologically active compound and a lipophilic counterion, and that is suitable for use with humans and/or animals without undue adverse side effects (such as toxicity, irritation, and allergic response) commensurate with a reasonable benefit/risk ratio.

The compositions of the present invention offer several advantages. The compositions are injectable compositions that contain high concentrations of the active compound. In preferred embodiments, the pharmacologically active compound may be loaded into the composition in the range of 10%–60% (w/v). But the person of ordinary skill in the art will realize this range may be varied widely, depending on the solubility or insolubility of the pharmacologically active compound, the lipophilic counterion selected, the solvent selected, the injectability of the final product, and any other relevant needs of the particular application. Active compound may also be loaded as low as 10%, or 5%, or even 1% and still provide a useful effect. Similarly, active compound may be loaded at 70%, or even higher as needs require. No exotic excipients or carriers are required. The compositions are easily filtered, thereby simplifying the manufacturing process. It is believed that the exclusion of water from the formulation should impart greater stability to the formulations, and inhibit the growth of microorganisms. The processes for preparing the compositions, as described herein, are simple, and administration according to the present invention should result in milder reactions at the injection site due to the neutralization of the pharmacologically active compound.

The present invention provides the ability to modulate the release rate and release time of the pharmacologically active compound. The release rate may be modulated by varying the lipophilicity and molecular weight of the counter-ion used to make the salt. For example, lauric acid salts of tilmicosin are usually released more slowly than decanoate salts. In addition, higher concentrations of the salt in the formulation usually yield slower release rates. The decanoate salt of tilmicosin is released more slowly from a 60% tilmicosin-fatty acid salt formulation that from a 30% tilmicosin-fatty acid salt formulation. Similarly, as explained herein, other variables such as selection of lipophilic counterion, solvent selection, salt concentration, and others may be manipulated to lengthen or shorten the release time of the active compound to the desired point. Generally, it may be desirable for salts to be based on the molar ratio of charged groups. But one may also successfully create insoluble salts by utilizing a hemi-salt or by otherwise varying from a 1:1 ratio. The pharmaceutically acceptable solvent may be a water miscible or water soluble solvent, and preferably may be a water miscible solvent. Mixtures of water soluble and/or water miscible solvents may also be utilized. The person of ordinary skill in the art will realize that various water soluble solvents may be mixed to optimize the result for a particular application. For example, a mixture of polyethylene glycol, propylene glycol, and glycerol formal may be mixed in various ratios to provide an optimal solvent. In some embodiments, mixing in approximately even amounts may provide a suitable solvent.

In other embodiments, formulations of the invention containing a salt of the pharmacologically active compound with a lipophilic counterion can be combined with the unsalted form of the active, in order to provide a greater initial dose of active compound.

Without wanting to be bound by any particular theory, injectable compositions may be obtained when a salt is formed of a pharmacologically active agent with a lipophilic counterion, and combined with a parenteral organic solvent. It is believed that when this formulation is injected into a mammal, the solvent may diffuse away from the injection site as aqueous body fluids diffuse towards the site, resulting in the precipitation of the pharmacologically active compound in the treated mammal. The precipitate may take many forms, for example, a solid, crystals, a gummy mass, or a gel. There will thus exist a concentration of the active compound that is released in a pharmaceutically effective amount over a desired period of time. The precipitate may act as a drug depot in the mammal resulting in the release of the compound over a period of time. Release times may be obtained of at least 3 days, at least 4 days, at least 5 days, at least 6 days at least 7 days, or any specific number of days up to and including at least 15 days, or even longer, as desired. By "drug depot" is meant a concentration or precipitation of pharmacologically active compound within the body of the treated mammal that releases a pharmaceutically effective amount of the active compound over time.

It was shown that the fatty acid chain length, the particular combinations of fatty acids, the percent pharmacologically active compound:lipophilic counterion salt in the formulation, and the pharmaceutically acceptable solvent selected all influence the release kinetics of the pharmacologically active compound. Thus, the release kinetics of the pharmacologically active compound may be conveniently and easily managed by manipulating these and other variables. It was also found that the formulations were stable to being sterilized by autoclave. The person of ordinary skill in the art will realize that the present invention may be applied to many pharmacologically active compounds that have an appropriate solubility and chemical functionality. Thus, it is contemplated that the present invention may be applicable to a wide variety of pharmacologically active compounds, such as drugs, medications, nutrients, or other desirable compounds for administration to a mammal.

The person of ordinary skill in the art will realize that some modifications to the methods presented herein may be desirable based on the particular characteristics of the pharmacologically active compound involved. The following non-limiting examples present further applications of the present invention and are provided by way of example only.

EXAMPLE 1

Oxytetracycline

Oxytetracycline has one tertiary amine group, and the hydrochloride salt of oxytetracycline is readily soluble in water. We have found that adding one mole of fatty acids to one mole of oxytetracycline creates a salt that has lower solubility in water but is more soluble than the starting oxytetracycline in N-methylpyrrolidone (NMP). When water is added to the NMP formulation, the salt precipitates.

Figure 1:
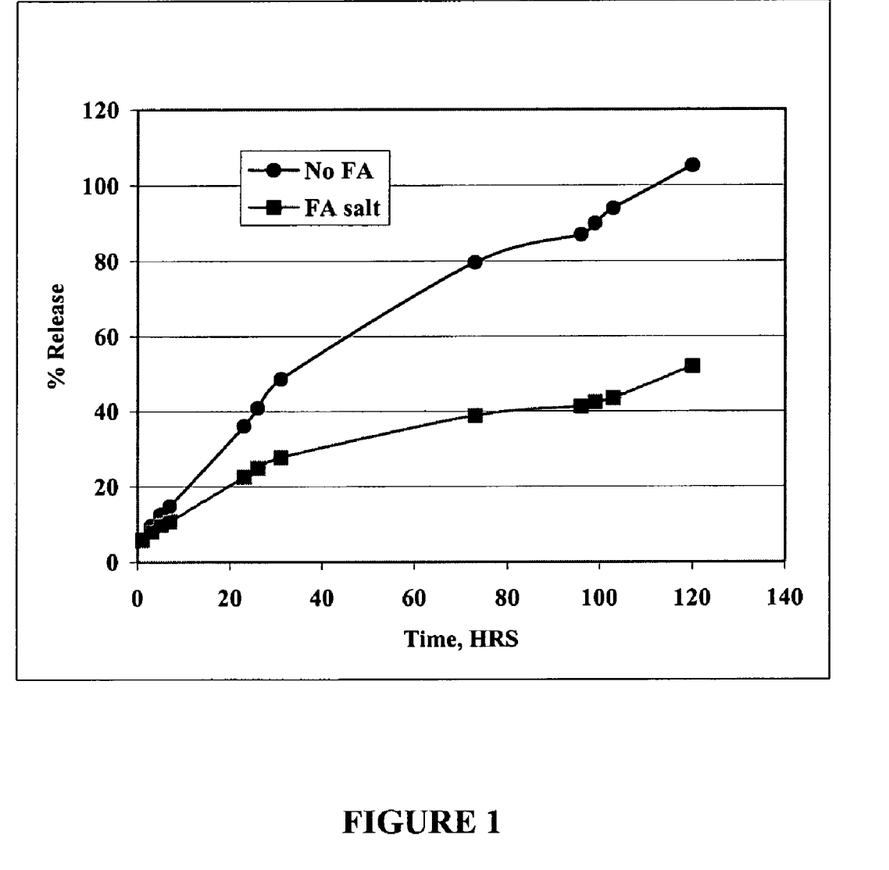
FIG. 1 is a graphical illustration showing that oxytetracycline prepared according to the present invention is released into saline at a rate slower than that of the free drug. The solvent is DMSO, and the lipophilic counterion is lauric acid.

The in vitro rate of release of oxytetracycline may be determined by sealing the formulation in a dialysis bag (Pierce, Rockford, Ill.), placing it in a reservoir of saline solution, and measuring the amount of drug in the saline as a function of time. The formulation of the present invention was compared with existing oxytetracycline formulations. FIG. 1 shows that the oxytetracycline formulation of the present invention is released into the saline at a rate substantially slower than that of the free drug.

An oxytetracycline composition according to the present invention was prepared by adding 0.464 grams of oxytetracycline and 0.203 grams of lauric acid to 3 ml of NMP. The mixture was stirred for 60 minutes, resulting in a clear solution. 1 ml of this solution was sealed in a dialysis bag, and the bag was suspended in 150 ml of phosphate-buffered saline, pH 7.4. Aliquots were removed at various intervals and oxytetracycline concentration was determined by spectrophotometry. The results in FIG. 1 show that oxytetracycline continued to diffuse out of the bag for more than 120 hours, at which point only about 50% of the oxytetracycline present had been released.

EXAMPLE 2

Metoprolol

Figure 2:
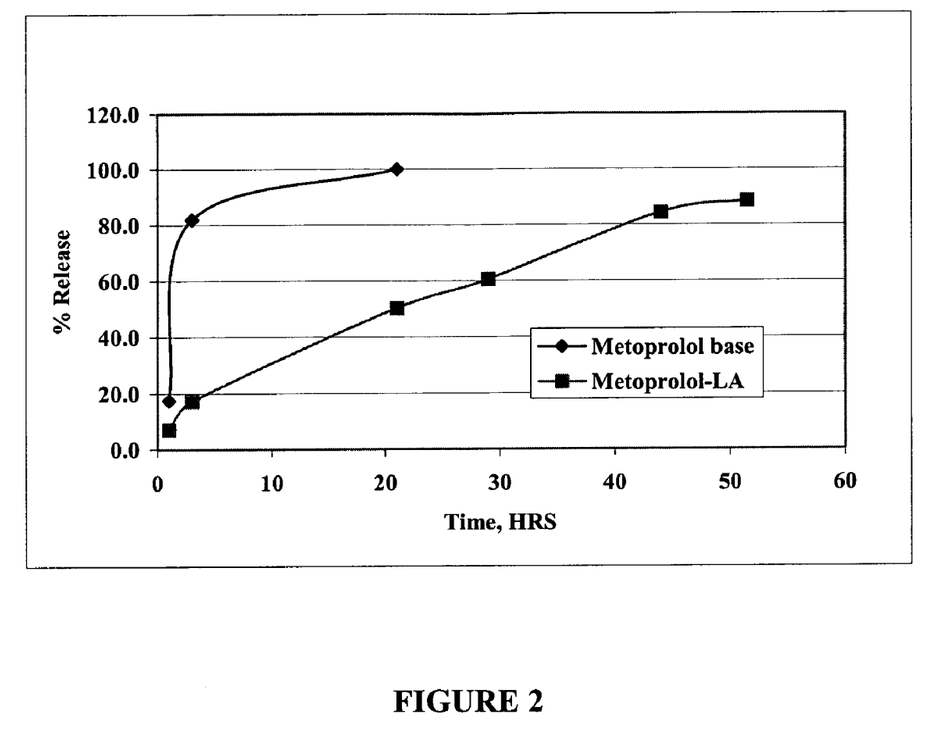
FIG. 2 is a graphical illustration showing that metoprolol prepared according to the present invention is released into saline at a rate slower than that of the free drug. Fatty acid and solvent are lauric acid and N-methylpyrrolidone.

Metoprolol is an antihypertensive, antianginal and antiarrhythmic drug, of the following structure:

Its succinate and tartarate salts are available commercially under several trade names. Both these salts as well as the base form of the drug are highly soluble in water. The base form of the metoprolol was prepared from commercially available tartarate salt by standard procedure. When the amine group of metoprolol is neutralized with lauric acid, the resulting salt is poorly soluble in water, but readily soluble in pharmaceutically-acceptable non-aqueous solvents. A metoprolol composition according to the present invention were prepared by adding 0.3224 grams of metoprolol base and 0.2661 grams of lauric acid to 2.415 ml of NMP. The mixture was stirred for 30 minutes, resulting in a clear solution. One ml of this solution was sealed in a dialysis bag, and the bag was suspended in 150 ml of phosphate-buffered saline, pH 7.4. Aliquots were removed at various intervals and metoprolol concentration was determined by spectrophotometry. The results in FIG. 2 show that metoprolol continued to diffuse out of the bag for more than 48 hours while the control solution of metoprolol base (prepared by dissolving 150 mg in 1.124 ml of NMP) is diffused off rapidly.

EXAMPLE 2A

Tilmicosin

Tilmicosin is an antibiotic in the macrolide class with the following structure:

It is effective against a broad range of bacteria, and is used for the treatment of respiratory diseases in cattle. The basic form is moderately soluble in aqueous solutions, while the chloride and phosphate salts are highly soluble. At elevated levels, tilmicosin is cardiotoxic, and therefore is not administered intravenously. For safety reasons, its use has been avoided almost entirely in sensitive species such as cats, goats, pigs, and horses.

Figure 4:
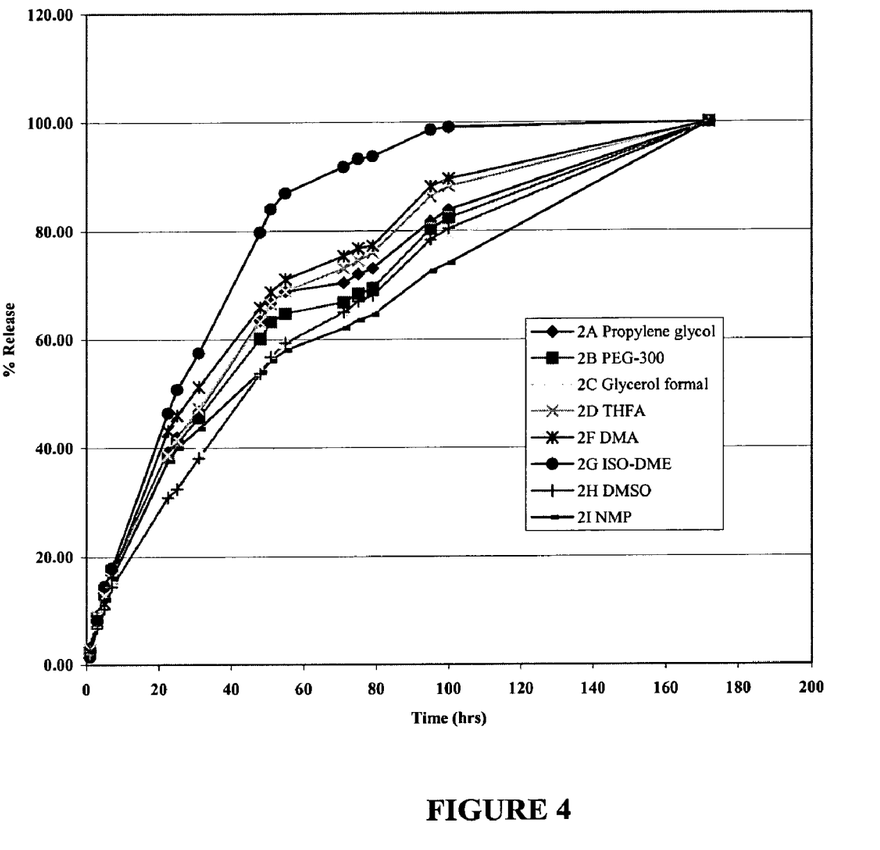
FIG. 4 is a graphical depiction illustrating the solvent effect on in vitro release kinetics in tilmicosin. Lipophilic counterion: di(decanoic) acid; tilmicosin at 100 mg/ml in the formulation. Abbreviations are as follows: PEG=polyethylene glycol, THFA=tetrahydro-furfuryl alcohol, DMA=dimethyl acetamide, ISO-DME=isosorbid dimethyl ether, DMSO=dimethyl sulfoxide, NMP=N-methyl pyrrolidone.
Figure 5:
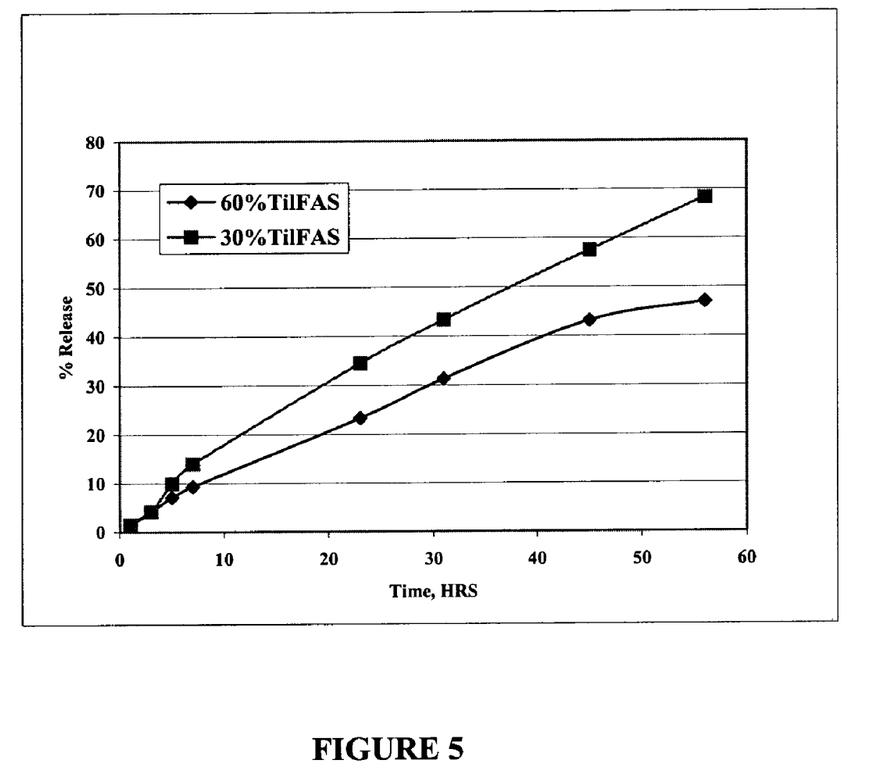
FIG. 5 is a graphical depiction illustrating that the rate of release of the pharmacologically active compound (tilmicosin) is a function of the concentration of fatty acid salt. Lipophilic counterion: decanoic acid.

When the two amine groups of tilmicosin are neutralized with any of several fatty acids (such as, for example, decanoic $C_{10}$, lauric $C_{12}$, myristic $C_{14}$, palmitic $C_{16}$, stearic $C_{18}$, Oleic $C_{18}$, elaidic $C_{18}$, linoleic $C_{18}$, and erucic $C_{22}$), the resulting salt is poorly soluble in water, but readily soluble in pharmaceutically-acceptable non-aqueous solvents. When the formulation of the salt is sealed in a dialysis cassette and place in saline, the tilmicosin salt precipitates, and tilmicosin is slowly released from the bag. The rate of release is a function of the chain length of the fatty acid (FIG. 3), the solvent (FIG. 4) and the tilmicosin-fatty acid salt concentration (FIG. 5).

EXAMPLE 3

Figure 3:
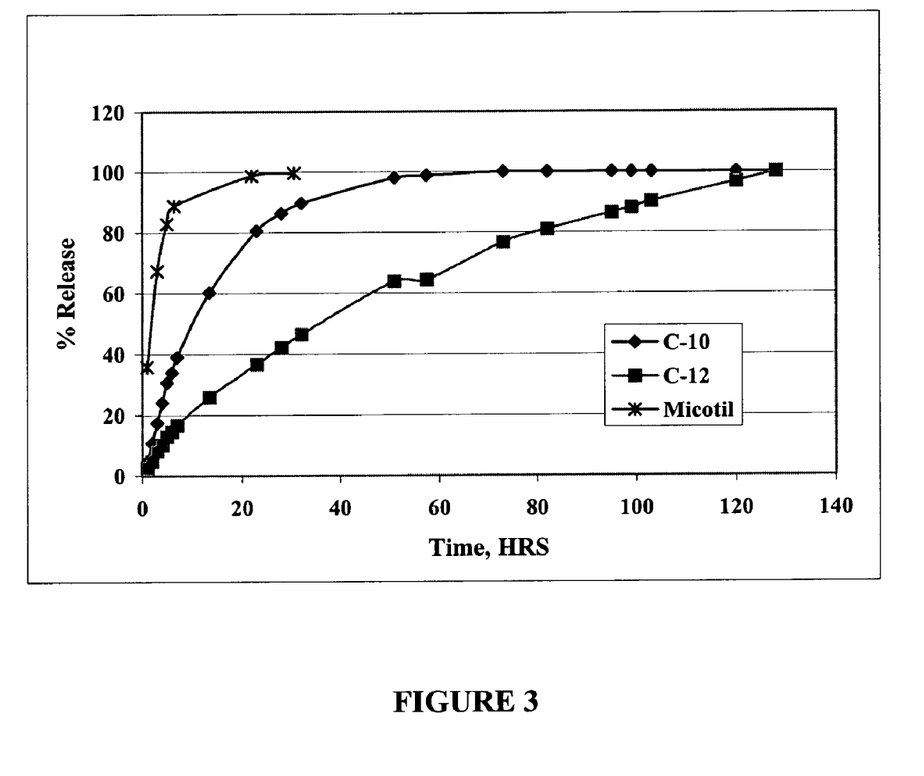
FIG. 3 is a graphical depiction illustrating that the rate of release of the pharmacologically active compound (tilmicosin) is affected by the chain length of the fatty acid selected. Solvent: N-methyl pyrrolidone; lipophilic counterion: decanoic acid and lauric acid.

Tilmicosin Salts in vitro 10 grams (0.0115 moles) of tilmicosin and 0.0253 moles of various carboxylic acids (such as, for example, decanoic, lauric, linoleic, or myristic acids, in individual assays) were taken in a flask and made up to a final volume of 100 ml with N-methyl-pyrrolidone and stirred for 60 minutes to obtain a clear solution. One ml aliquots of these solutions were sealed in dialysis bags, and the bags were suspended in flasks containing 150 ml of phosphate-buffered saline, pH 7.4. The salt was observed to precipitate in the bag within about 1 hour. Aliquots of saline were removed at various intervals and tilmicosin was determined by HPLC. The results with decanoic acid (C-10) and lauric acid (C-12) salts in FIG. 3 show that tilmicosin continued to diffuse out of the bag for more than 120 hours. Longer chain length acids caused a slower release of tilmicosin. Micotil® (Eli Lilly, Indianapolis, Ind.), a phosphate salt of tilmicosin, is readily soluble and rapidly diffuses from the bag.

EXAMPLE 4

Tilmicosin-di(decanoic acid) in Various Solvents

Solutions of tilmicosin di(decanoic acid) salt were prepared in several water-miscible solvents, combining 10 grams (0.0115 moles) of tilmicosin and 0.0253 moles of decanoic acid in various solvents to a final volume of 100 ml. The in vitro release rates were measured using the dialysis method of Example 1. The results in FIG. 4 show that the release rate varies with the solvent, but that all of the solvents yield a slower release rate than that observed with the phosphate salt (Micotil(R)) shown in FIG. 3.

EXAMPLE 5

Tilmicosin Release Concentration Effect

Solutions of tilmicosin di(decanoic acid) salt were prepared by combining 30 grams (0.0345 moles) or 60 grams (0.0690 moles) of tilmicosin with 2 equivalents of decanoic acid in NMP to a final volume of 100 ml. The in vitro release rates were measured using the dialysis method of Example 1, and the data in FIG. 5 show that higher starting concentrations result in a slower release rate.

EXAMPLE 6

Tilmicosin in vivo

Formulations of tilmicosin didecanoate, dilaurate, and dimyristate were formulated at 100 mg/ml in N-methyl pyrrolidone and subcutaneously injected into cats in the back of the neck at a dosage of 45 or 75 mg/kg of body weight. Previous data indicates that a dosage of 25 mg/kg of the phosphate salt of tilmicosin is fatal to cats. The cats showed hypothermia and lethargy after injection, indicative of the bioavailability of the drug. The toxicity was found to be substantially less in formulations with fatty acid chain lengths greater than $C_{10}$, consistent with the slower release of drug from these formulations. All of the cats survived and were behaving normally 3 days after the injection. The results are summarized in the following Table 1.

Table 1: Blood Levels of Tilmicosin at Specific Time Intervals 100 mg/ml of a formulation of a salt of tilmicosin with decanoic acid, lauric acid, or myristic acid in N-methyl pyrrolidone were injected into 9 healthy adult cats at the dosages indicated. The resulting concentrations in blood cells and plasma for each individual cat at 6 hours and 2 days are shown in Table 1.

| Cat No. | Fatty Acid | Dosage | 6 hrs Blood cells (µg/ml) | 6 hrs Plasma (µg/ml) | Day 2 Blood cells (µg/ml) | Day 2 Plasma (µg/ml) |
|---|---|---|---|---|---|---|
| 1 | C-12 | 45 mg/kg | 5.8 | 11.3 | 0.9 | 0.5 |
| 2 | C-12 | 75 mg/kg | 5.5 | 18.0 | 1.5 | 1.5 |
| 3 | C-12 | 75 mg/kg | 2.5 | 9.9 | 0.9 | 1.0 |
| 4 | C-14 | 45 mg/kg | 2.4 | 7.5 | 0.9 | 1.1 |
| 5 | C-14 | 75 mg/kg | 6.7 | 11.6 | 9.1 | 4.6 |
| 6 | C-14 | 75 mg/kg | 3.5 | 6.1 | 1.5 | 0.7 |
| 7 | C-10 | 45 mg/kg | 3.7 | 15.9 | | |
| 8 | C-10 | 75 mg/kg | 4.2 | 18.4 | | |
| 9 | C-10 | 45 mg/kg | 3.3 | 9.1 | | |

Tilmicosin salts were also studied in tissue. A tilmicosin:dilauric fatty acid salt in 10% propylene glycol in glycerol formal at 100 mg/ml was administered subcutaneously at 10 mg/kg dose and the biodistribution in cats was determined.

The methods described here were developed for the determination and quantification of tilmicosin in various animal tissues and serum, particularly feline liver, kidney and lung tissue and serum. The person of ordinary skill in the art will realize that many variations of the methods described here are possible without departing from the invention.

Figure 8:
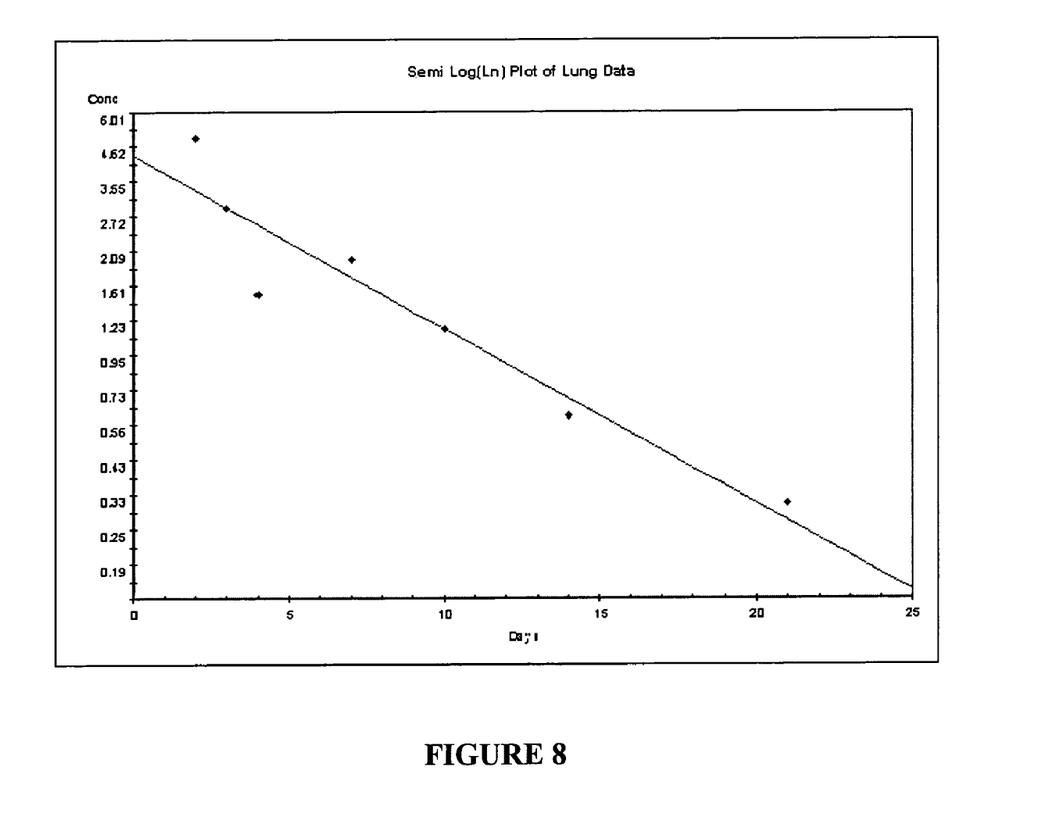
FIG. 8 is a semilog plot of tilmicosin concentration in cat lung tissue over 21 days. Eight male and eight female cats were used and dosed with 10 mg/kg of body weight for all tissue types.
Figure 9:
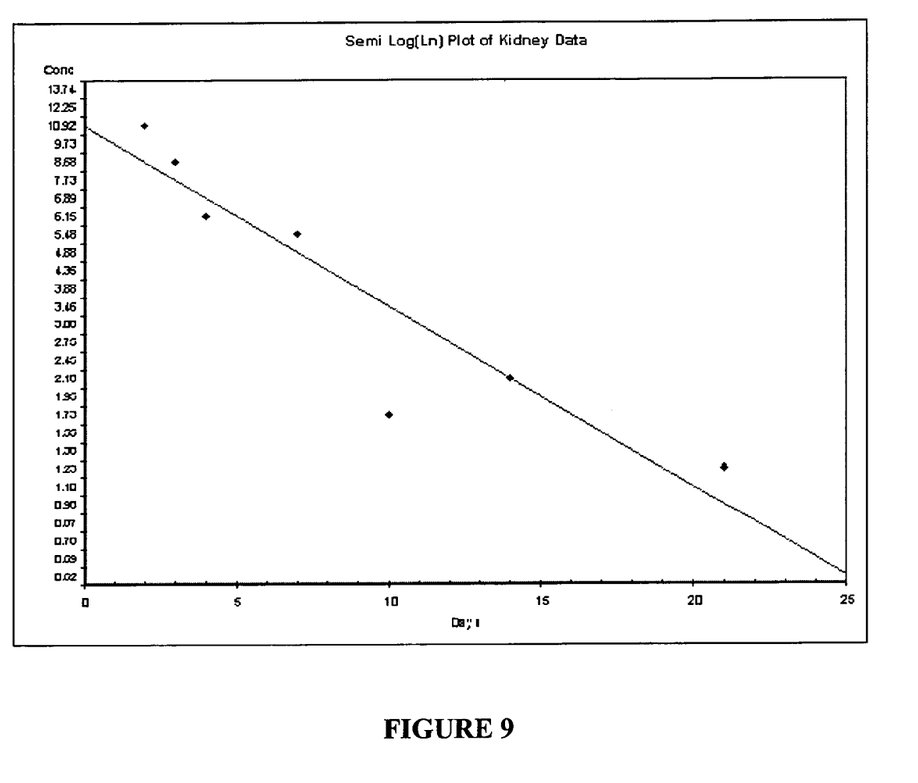
FIG. 9 is a semilog plot of tilmicosin concentration in cat kidney tissue over 21 days. Eight male and eight female cats were used and dosed with 10 mg/kg of body weight for all tissue types.
Figure 10:
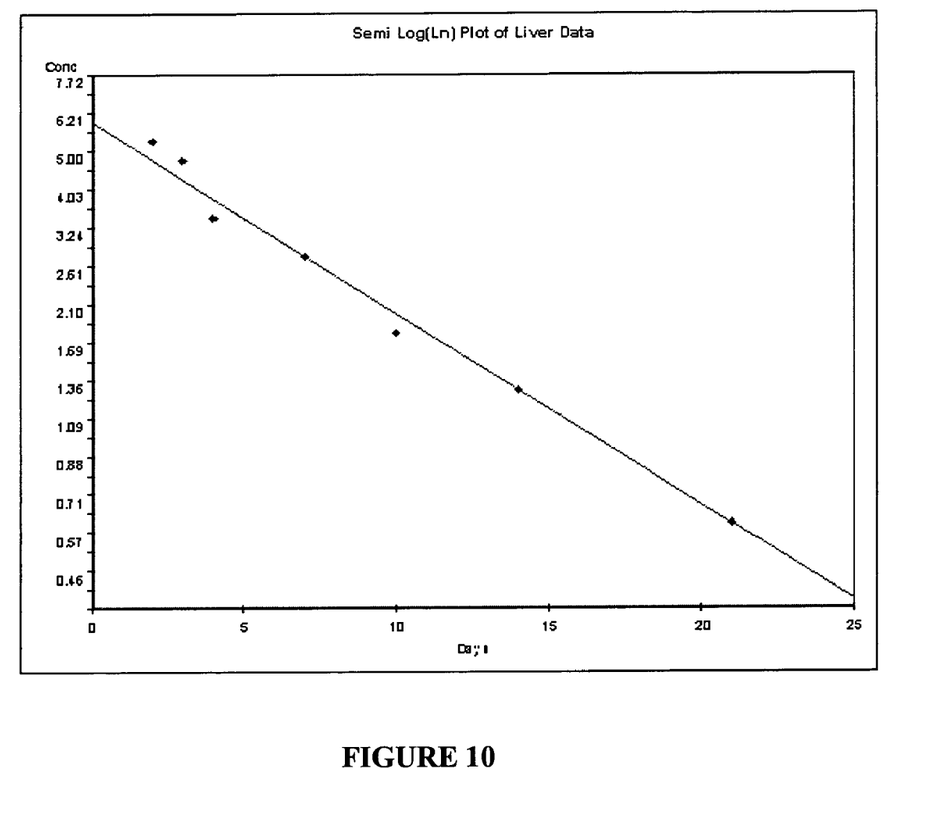
FIG. 10 is a semilog plot of tilmicosin concentration in cat liver tissue over 21 days. Eight male and eight female cats were used and dosed with 10 mg/kg of body weight for all tissue types.

The kidney, liver and lung tissue samples were collected 2, 3, 4, 7, 14, and 21 days after injecting the animals with tilmicosin formulation at 10 mg/kg of body weight. The results are presented in FIGS. 8, 9 & 10. It was found that kidney is the marker tissue in cats while the liver is the marker in cows and pigs. The levels in kidney were consistently higher than in liver with Cmax (kidney: 13.8 mcg/gm; Liver: 7.3 mcg/gm) reached around 48 hours in both tissues. The Cmax for lung was found to be 7.5 mcg/gm and was observed around 48 hours after injecting the dose. Detectable levels of tilmicosin persisted in tissues through day 21 of the study.

A drug extraction efficiency of ~98% was obtained at a concentration of 1 mcg/gm of tissue. The limit of detection for tilmicosin in various feline tissues was determined to be 0.032 mcg/gm. For feline serum, a drug extraction efficiency of 95% was obtained over a concentration range of 0.15 to 6 mcg/ml after fortification. The limit of detection was determined to be 0.16 mcg/ml with linearity extending from 0.15 to 6 mcg/ml.

Preparation of Tissue Samples

Tissue samples were prepared by mincing with scissors or a scalpel on a paper towel. 10 ml of methanol was added to each tube and the samples homogenized separately for 10 to 15 minutes. Samples were sonicated on ice for one minute and centrifuged at 10,000 rpm for 30 minutes at 4 C. The methanol extract was decanted into fresh centrifuge tubes and the tissue samples resuspend in the tubes with 10 mL of methanol and 5.0 mL of 100 mM phosphate. The tubes were vortexed and centrifuged at 10,000 rpm for 30 minutes at 4 C. The extract was decanted into fresh centrifuge tubes and centrifuged at 5000 rpms for 10 minute at 4 C. The methanol extract was added to 70 mL of water in a flask and swirled in the flask to mix.

Each pool of extracts was loaded to a solid phase extraction $C_{18}$ Sep-Pak Plus® (SPE) cartridge (Waters, Milford, Mass.) using a vacuum manifold or hydrostatic pump to draw the pools through the cartridges. Once sample were completely loaded, each SPE cartridge was washed with 10 mL of water, and then with 10 mL of 25% acetonitrile/water at a flow rate of less than 5 mL/minute. The SPE cartridges were disconnected from the apparatus and dried completely under high vacuum (26 in. Hg) in a vacuum desiccation jar for 10 minutes.

Analyte was eluted from the SPE cartridges with 5% acetic acid/methanol. Only the first 2.0 mL of eluate was collected. The volumetric flasks were inverted and mixed, and stored overnight at 4 C.

The sample eluates were filtered through a 0.22 um PVDF filter, and analyzed by HPLC on a SphereClone® 5 um phenyl column (Phenomenex, Torrance, Calif.).

EXAMPLE 7

Fluoxetine

Figure 6:
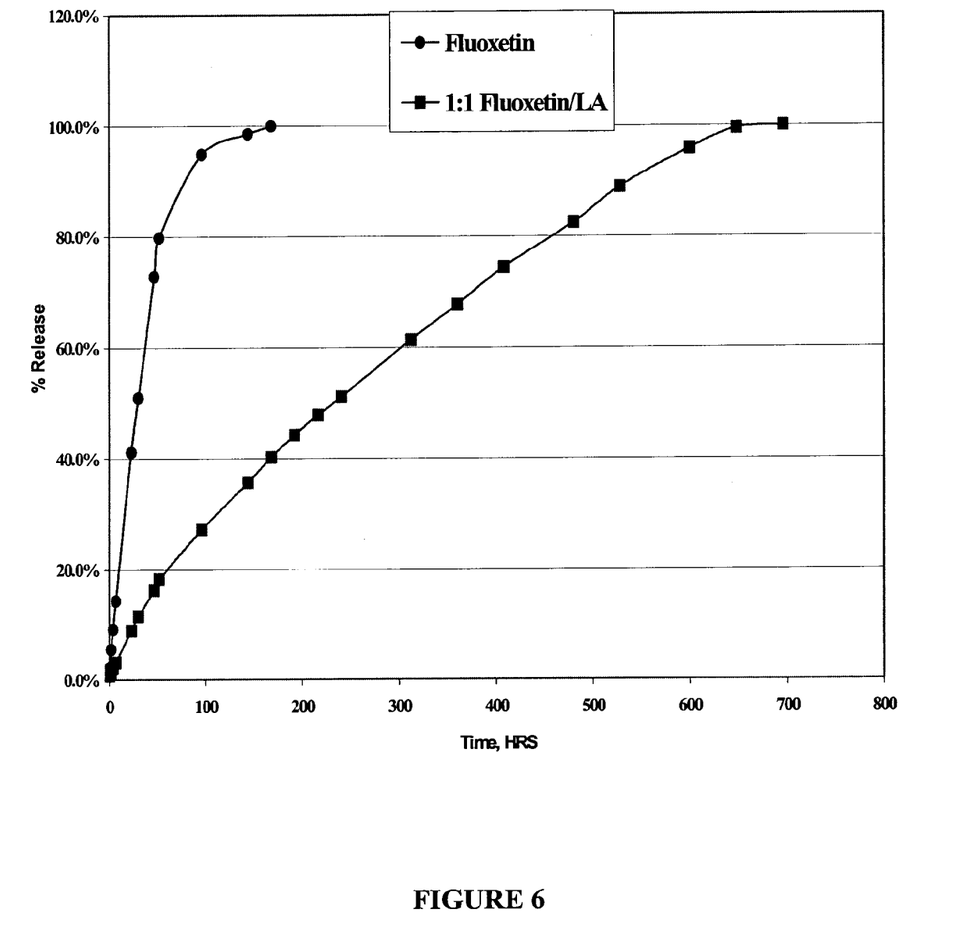
FIG. 6 is a graphical depiction illustrating the in vitro release kinetics of fluoxetine:lauric acid fatty acid salt formulation.

Fluoxetine is a selective serotonin reuptake inhibitor and is extensively used to treat psychological disorders such as obsessive-compulsive disorder in humans. It is shown that fluoxetine is effective for treating aggressive behavior and separation anxiety in dogs and urine spraying behavior in cats. Fluoxetine is formulated at 100 and 150 mg/ml as a lauric acid salt in 10% propylene glycol in glycerol formal in 1:1 drug to fatty acid ratio. In vitro release kinetics were studied for both formulations at 100 mg/mL concentration using the dialysis technique described in Example 1, and the results presented in FIG. 6. Fluoxetine base in 10% propylene glycol in glycerol formal at 100 mg/ml is used as a control in the experiment. While the fluoxetine base formulation is released for about 160 hrs, the 1:1 (drug:LA) lauric acid salt formulation was released for 700 hrs.

Figure 7:
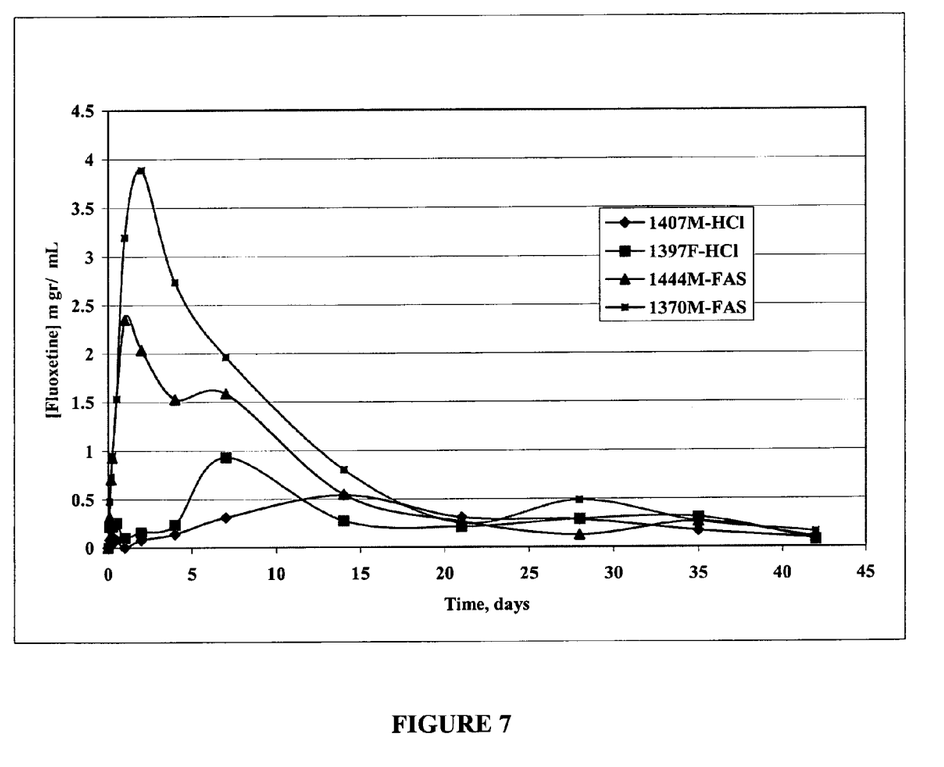
FIG. 7 is a graphical depiction of the pharmacokinetics of fluoxetine hydrochloride (HCl) and fluoxetine:lauric acid fatty acid salt (FAS) in cats.

The fatty acid salt formulation with 1:1.1 fluoxetine to lauric acid ratio at 150 mg/mL concentration was injected sub cutaneous into cats at 20 and 30 mg/kg. At the same time two cats were dosed at 1 mg/kg/day orally for 28 days. Serum samples were collected through day 42 and analyzed for fluoxetine by HPLC using 35% acetonitrile in phosphate buffer, pH 2.7 on a $C_{18}$ column. The results suggest that a single sub cutaneous injection of fatty acid salt formulation provide drug concentrations comparable to daily oral dose through 42 days (FIG. 7).

The fluoxetine was also formulated as linoleic acid salt in 10% propylene glycol in glycerol formal, yielding a clear solution. This formulation was also found to precipitate in water.

EXAMPLE 8

Roxithromycin

Roxithromycin is an antibiotic in the macrolide class with the following structure:

It is effective against a broad range of bacteria, and is used for the treatment of respiratory diseases in cattle. The amine group of roxithromycin was neutralized with linoleic acid in 10% propylene in glycerol formal, resulting in a clear solution at 200 mg/ml. As in the case of tilmicosin, the salt precipitated when the solution was spiked in water.

EXAMPLE 9

Terbinafine

Terbinafine is an antifungal and the structure is as shown below:

Terbinafine is a specific inhibitor of squaline epoxidase, a key enzyme in fungal ergosterol biosynthesis. The amine group of terbinafine was neutralized with linoleic acid in 10% propylene glycol in glycerol formal, resulting in a clear solution at 150 mg/ml. The resulting salt was highly insoluble in water, and precipitated when spiked into water.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A composition comprising:
   a di-lauric acid salt of tilmicosin and a pharmaceutically acceptable solvent;
   wherein at least a portion of the di-lauric acid salt of tilmicosin is dissolved in the solvent, the composition is injectable, and the composition forms a precipitate when injected into water.

2. A composition according to claim 1 wherein the pharmaceutically acceptable solvent comprises about 90% glycerol formal and about 10% propylene glycol.

3. A composition according to claim 1 wherein the pharmaceutically acceptable solvent comprises N-methyl pyrrolidone.

4. The composition of claim 1, wherein the pharmaceutically acceptable solvent is selected from the group consisting of pyrrolidone, N-methyl pyrrolidone, polyethylene glycol, propylene glycol, glycerol formal, isosorbid dimethyl ether, ethanol, dimethyl sulfoxide, tetrahydrofufuryl alcohol, triacetin, and combinations thereof.

5. The composition of claim 2 having a tilmicosin concentration that ranges from about 100 mg/ml to about 600 mg/ml.

6. The composition of claim 2 having a tilmicosin concentration that is about 100 mg/ml.

7. A method of treating a bacterial infection in a mammal comprising:
   injecting the mammal with the composition of claim 1 having a tilmicosin concentration of about 100 mg/ml at a dose of about 10 mg tilmicosin/kg of the mammal.

8. The method according to claim 7 wherein the mammal is a dog or a cat.

9. The method according to claim 7 wherein the mammal is a domestic cat.

10. A composition comprising:

a di-decanoic acid salt of tilmicosin and a pharmaceutically acceptable solvent;

wherein at least a portion of the di-decanoic acid salt of tilmicosin is dissolved in the solvent, the composition is injectable, and the composition forms a precipitate when injected into water.

11. A composition according to claim 10 wherein the pharmaceutically acceptable solvent comprises about 90% glycerol formal and about 10% propylene glycol.

12. A composition according to claim 10 wherein the pharmaceutically acceptable solvent comprises N-methyl pyrrolidone.

13. A method of treating a bacterial infection in a mammal comprising:

injecting the mammal with the composition of claim 10 having a tilmicosin concentration ranging from about 100 mg/ml to about 600 mg/ml at a dose ranging from about 10 mg tilmicosin/kg of the mammal to about 45 mg tilmicosin/kg of the mammal.

14. The method according to claim 13 wherein the composition has a tilmicosin concentration of about 300 mg/ml.

15. The method according to claim 13 wherein the mammal is a dog or a cat.

16. The method of claim 15 wherein the mammal is a domestic cat.

17. The composition of claim 10, wherein the pharmaceutically acceptable solvent is selected from the group consisting of pyrrolidone, N-methyl pyrrolidone, polyethylene glycol, propylene glycol, glycerol formal, isosorbid dimethyl ether, ethanol, dimethyl sulfoxide, tetrahydrofufuryl alcohol, triacetin, and combinations thereof.

18. The composition of claim 11 having a tilmicosin concentration that ranges from about 100 mg/ml to about 600 mg/ml.

19. The composition of claim 11 having a tilmicosin concentration that is about 100 mg/ml.

20. A method of treating a bacterial infection in a mammal comprising:

injecting the mammal with the composition of claim 1 having a tilmicosin concentration ranging from about 100 mg/ml to about 600 mg/ml at a dose ranging from about 10 mg tilmicosin/kg of the mammal to about 45 mg tilmicosin/kg of the mammal.

21. The method according to claim 20 wherein the composition has a tilmicosin concentration of about 300 mg/ml.

22. The method according to claim 20 wherein the mammal is a dog or a cat.

23. The method of claim 22 wherein the mammal is a domestic cat.

24. A method of treating a bacterial infection in a mammal comprising:
    injecting the mammal with the composition of claim 10 having a tilmicosin concentration of about 100 mg/ml at a dose of about 10 mg tilmicosin/kg of the mammal.

25. The method according to claim 24 wherein the mammal is a dog or a cat.

26. The method according to claim 24 wherein the mammal is a domestic cat.

27. A composition comprising:
    a di-lauric acid salt of tilmicosin and a pharmaceutically acceptable solvent;
    wherein the di-lauric acid salt of tilmicosin is dissolved in the solvent and the composition forms a precipitate when injected into water.

28. The composition of claim 27, wherein the pharmaceutically acceptable solvent is selected from the group consisting of pyrrolidone, N-methyl pyrrolidone, polyethylene glycol, propylene glycol, glycerol formal, isosorbid dimethyl ether, ethanol, dimethyl sulfoxide, tetrahydrofufuryl alcohol, triacetin, and combinations thereof.

29. A composition according to claim 27 wherein the pharmaceutically acceptable solvent comprises about 90% glycerol formal and about 10% propylene glycol.

30. A composition according to claim 27 wherein the pharmaceutically acceptable solvent comprises N-methyl pyrrolidone.

31. A method of treating bacterial infection in a mammal comprising:
    injecting the mammal with the composition of claim 27 having a tilmicosin concentration ranging from about 100 mg/ml to about 600 mg/ml at a dosage ranging from about 10 mg tilmicosin/kg of mammal to about 45 mg tilmicosin/kg of the mammal.

32. The method according to claim 31 wherein the composition has a tilmicosin concentration of about 300 mg/ml.

33. The method according to claim 31 wherein the mammal is a dog or a cat.

34. The method according to claim 33 wherein the mammal is a domestic cat.

35. A method of treating a bacterial infection in a mammal comprising:
    injecting the mammal with the composition of claim 27 having a tilmicosin concentration of about 100 mg/ml at a dose of about 10 mg tilmicosin/kg of the mammal.

36. The method according to claim 35 wherein the mammal is a dog or a cat.

37. The method according to claim 36 wherein the mammal is a domestic cat.

38. A composition comprising:
    a di-decanoic acid salt of tilmicosin and a pharmaceutically acceptable solvent;
    wherein the di-decanoic acid salt of tilmicosin is dissolved in the solvent and the composition forms a precipitate when injected into water.

39. The composition of claim 38, wherein the pharmaceutically acceptable solvent is selected from the group consisting of pyrrolidone, N-methyl pyrrolidone, polyethylene glycol, propylene glycol, glycerol formal, isosorbid dimethyl ether, ethanol, dimethyl sulfoxide, tetrahydrofufuryl alcohol, triacetin, and combinations thereof.

40. A composition according to claim 38 wherein the pharmaceutically acceptable solvent comprises about 90% glycerol formal and about 10% propylene glycol.

41. A composition according to claim 38 wherein the pharmaceutically acceptable solvent comprises N-methyl pyrrolidone.

42. A method of treating a bacterial infection in a mammal comprising:
    injecting the mammal with the composition of claim 38 having a tilmicosin concentration ranging from about 100 mg/ml to about 600 mg/ml at a dosage ranging from about 10 mg tilmicosin/kg of the mammal to about 45 mg tilmicosin/kg of the mammal.

43. The method according to claim 42 wherein the composition has a tilmicosin concentration of about 300 mg/ml.

44. The method according to claim 42 wherein the mammal is a dog or a cat.

45. The method according to claim 44 wherein the mammal is a domestic cat.

46. A method of treating a bacterial infection in a mammal comprising:
    injecting the mammal with the composition of claim 38 having a tilmicosin concentration of about 100 mg/ml at a dose of about 10 mg tilmicosin/kg of the mammal.

47. The method according to claim 46 wherein the mammal is a dog or a cat.

48. The method according to claim 47 wherein the mammal is a domestic cat.

* * * * *